United States Patent [19]
Kalvoda et al.

[11] Patent Number: 5,317,100
[45] Date of Patent: May 31, 1994

[54] PROCESS FOR THE PREPARATION OF OPTICALLY ACTIVE ACYLOXYAZETIDINONES

[75] Inventors: Jaroslav Kalvoda, Binningen, Switzerland; Martin Kessler, Hausgauen, France; René Lattmann, Binningen; Gerardo Ramos, Arlesheim, both of Switzerland

[73] Assignee: Ciba-Geigy Corp., Ardsley, N.Y.

[21] Appl. No.: 964,818

[22] Filed: Oct. 22, 1992

Related U.S. Application Data

[63] Continuation of Ser. No. 780,833, Oct. 23, 1991, abandoned, which is a continuation of Ser. No. 678,891, Mar. 28, 1991, abandoned, which is a continuation of Ser. No. 427,080, Oct. 25, 1989, abandoned.

[30] Foreign Application Priority Data

Nov. 4, 1988 [CH] Switzerland .................. 4115/88-0

[51] Int. Cl.$^5$ .................. C07D 205/08; C07D 303/48; C07B 41/12
[52] U.S. Cl. ........................ 540/357; 540/200; 549/548; 435/121
[58] Field of Search .................. 540/357; 435/121

[56] References Cited

U.S. PATENT DOCUMENTS

| | | | |
|---|---|---|---|
| 3,452,000 | 6/1969 | Testa et al. | 260/239 |
| 4,260,627 | 4/1981 | Christensen | 540/200 |
| 4,871,841 | 10/1989 | Ermann | 540/364 |
| 4,882,429 | 11/1989 | McCombie | 540/357 |

FOREIGN PATENT DOCUMENTS

| | | | |
|---|---|---|---|
| 0078026 | 5/1983 | European Pat. Off. | |
| 221846 | 5/1987 | European Pat. Off. | 540/357 |
| 240164 | 10/1987 | European Pat. Off. | |
| 159501 | 2/1970 | Fed. Rep. of Germany | |
| 2046823 | 3/1972 | Fed. Rep. of Germany | |
| 2842466 | 4/1979 | Fed. Rep. of Germany | |

OTHER PUBLICATIONS

Hanessian, J. Am. Chem. Soc. 107, 1438 (1985).
Sohar, Appl. Microbiol. Biotechnol. 27, 451–456 (1988).
Webber, Chem. Abst. 76, 140851x (1972).
Johnson, Chem. Abst. 90, 103514h (1978).
Sumitomo, Chem. Abst. 94, 139373s (1980).
Inst. Physical and Chem. Res., Chem. Abst. 94, 192502a (1980).
Komendantov, Chem. Abst. 104, 224577 (1985).
Terajima, Chem. Abst. 108, 131830s (1987).
Geiger "The Peptides" (Academic Press, Inc. 1981) vol. 3, pp. 6–7.
McCombie "Protective Groups in Organic Synthesis", (1973) p. 48.
Gould, "Mechanism & Structure in Organic Chemistry", pp. 317–318 (1959).
March, Adv. Org. Chemistry 3rd Ed. (1985) p. 298.
*Chem Abstr.* 89, 1978, 197031c, Momose.
House, "Modern Synthetic Reactions", 2nd Ed. pp. 321–328, 1972.
Yao, Analytica Chemica Acta 207, 319–323 (1988).
Sankyo Chem. Abstr. 103, 123272t, 1985.
Derwent Abstr. for EP 181,831, published 1986.

*Primary Examiner*—Mark L. Berch
*Attorney, Agent, or Firm*—Irving M. Fishman; Karen G. Kaiser

[57] ABSTRACT

Compounds of the formula

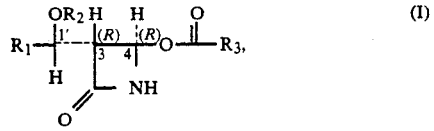

in which $R_1$ is hydrogen or lower alkyl, $R_2$ is hydrogen or a hydroxyl protective group $R_2'$ and $R_3$ is substituted or unsubstituted phenyl or lower alkyl can be prepared in a three-stage process from readily accessible β-lactam starting materials.

11 Claims, No Drawings

PROCESS FOR THE PREPARATION OF OPTICALLY ACTIVE ACYLOXYAZETIDINONES

This application is a continuation of Ser. No. 07/780,833, filed Oct. 23, 1991, now abandoned, which is a continuation of Ser. No. 07/678,891, filed Mar. 28, 1991, now abandoned, which is a continuation of Ser. No. 07/427,080, filed Oct. 25, 1989, now abandoned.

The present invention relates to a process for the preparation of 3,4-trans-disubstituted azetidinones of the formula

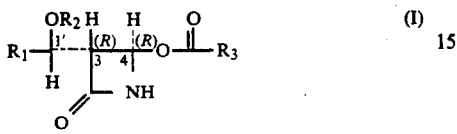

in which $R_1$ is hydrogen or lower alkyl, $R_2$ is hydrogen or a hydroxyl protective group $R_2'$ and $R_3$ is substituted or unsubstituted phenyl or lower alkyl.

The general definitions used within the scope of this invention preferably have the following meanings:

Groups or compounds marked "lower" preferably contain up to and including 7, preferably up to and including 4 carbon atoms.

As lower alkyl, $R_1$ is preferably methyl and also ethyl, n-propyl, isopropyl, n-butyl, isobutyl or tert-butyl. $R_1$ is primarily methyl and also hydrogen.

Hydroxyl protective groups $R_2'$, including their introduction and removal, are described, for example, in "Protective Groups in Organic Chemistry", Plenum Press, London and New York 1973, and also in "Protective Groups in Organic Chemistry", Wiley, New York 1974. A hydroxyl protective group is, for example, the acyl radical of a carboxylic acid, for example lower alkanoyl which is substituted by halogen, such as fluorine or chlorine, for example 2,2-dichloroacetyl or 2,2,2-trifluoroacetyl, or a benzoic acid which is unsubstituted or substituted, for example, by nitro, halogen, such as chlorine, or lower alkoxy, such as methoxy, for example benzoyl or 4-nitrobenzoyl, 3,5-dinitrobenzoyl, 4-chlorobenzoyl or 4-methoxybenzoyl, and also the acyl radical of a carbonic acid lower alkyl or lower alkenyl half-ester which is unsubstituted or substituted, for example, by halogen, such as chlorine, or by phenyl which can contain substituents, such as 4-nitrophenyl, for example 2,2,2-tiichloroethoxycarbonyl, allyloxycarbonyl, benzyloxycarbonyl or 4-nitrobenzyloxycarbonyl, or the acyl radical of an organic sulfonic acid, for example lower alkanesulfonyl, such as methanesulfonyl, or arylsulfonyl, such as toluenesulfonyl. Hydroxyl protective groups are also 2-oxacycloalkyl or 2-thiacycloalkyl having 5 or 6 ring atoms, for example 2-tetrahydrofuryl or 2-tetrahydropyranyl, and also a thia analogue thereof, 1-lower alkyloxy-lower alkyl, for example methoxymethyl or 1-ethoxyethyl, or silyl which is trisubstituted, in particular, by lower alkyl, aryl-lower alkyl and/or aryloxy, for example tri-lower alkylsilyl, such as trimethylsilyl, triethylsilyl, dimethyl-(2-ethyl-2-propyl)-silyl, diethyl-(2-ethyl-2-propyl)-silyl, dimethyl-(tert-butyl)-silyl or dimethyl-(2,3-dimethyl-2-butyl)-silyl, diaryl-(lower alkyl)-silyl, for example diphenyl-(tert-butyl)-silyl, aryl-(di-lower alkyl)-silyl, for example tert-butylmethylphenylsilyl, and di-lower alkyl-(lower alkylphenoxy)-silyl, for example dimethyl-(2,4,6-tri-tert-butylphenoxy)-silyl. Protective groups $R_2'$ which are particularly preferred because of their stability to bases and hydrolysis are trialkylsilyl, in particular trimethylsilyl, tert-butyldimethylsilyl or dimethyl-(2,3-dimethyl-2-butyl)-silyl.

As substituted phenyl, $R_3$ is phenyl which is substituted, preferably monosubstituted to trisubstituted, for example by lower alkoxy, for example methoxy, lower alkyl, for example methyl and/or halogen, for example chlorine, for example 4-methoxyphenyl, 4-nitrophenyl, 2-, 3- or 4-chlorophenyl or 4-tolyl. As lower alkyl, $R_3$ is, for example, ethyl, n-propyl, isopropyl, n-butyl, isobutyl or tert-butyl, especially methyl. $R_3$ is preferably phenyl and methyl.

The process according to the invention comprises
(a) treating a compound of the formula

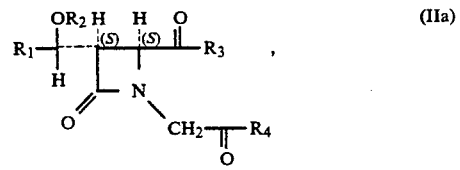

in which $R_4$ is substituted or unsubstituted phenyl or lower alkyl with a peracid, or decarboxylating by acyloxylation a compound of the formula

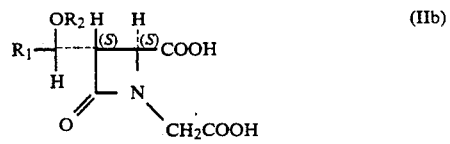

with the introduction of the radicals $R_3-C(=O)-$ or $R_4-C(=O)-$, (b) replacing the radical of the formula $R_4-C(=O)-$ by hydrogen in a compound of the formula

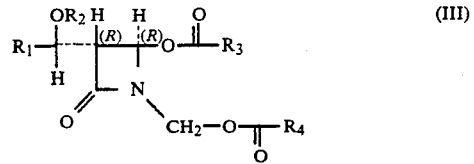

obtainable as in (a), and (c) removing, in a compound of the formula

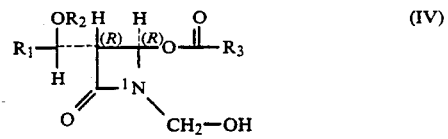

thus obtainable, the hydroxymethyl group in the 1-position, if appropriate after conversion into a formyl group, and, if desired, in a compound of the formula I thus obtainable in which $R_2$ is a protective group $R_2'$, converting the protected hydroxyl group into the free hydroxyl group, and/or, if desired, in a compound of the formula I thus obtainable in which $R_2$ is hydrogen, converting the free hydroxyl group into a protected hydroxyl group.

Preferred starting materials are those of the formulae IIa or IIb in which $R_1$ is hydrogen or methyl, $R_2$ is hydrogen or a hydroxyl protective group $R_2'$, such as dimethyltert-butylsilyl or dimethyl-(2,2-dimethyl-2-butyl)-silyl, and $R_3$ and $R_4$, preferably both identical, are phenyl or methyl.

The treatment of the starting material of the formula IIa with a peracid is preferably carried out by the Baeyer-Villiger reaction, in which organic or inorganic peracids or salts thereof, such as alkali metal or alkaline earth metal salts, for example sodium, potassium or magnesium salts, can be employed. Organic peracids are, in particular, the corresponding percarboxylic acids, inter alia lower alkanepercarboxylic acids which are unsubstituted or substituted, for example, by halogen, such as peracetic acid or trifluoroperacetic acid or trihalogenoiminoperacetic acid, for example trichloroiminoperacetic acid or trifluoroiminoperacetic acid, aromatic peracids which are unsubstituted or substituted, for example, by nitro and/or halogen, such as perbenzoic acid, 4-nitroperbenzoic acid, 3-chloroperbenzoic acid, 3,5-dinitroperbenzoic acid or monoperphthalic acid, or a salt thereof, for example magnesium monoperphthalate. Examples of inorganic peracids are peroxosulfuric acids, such as peroxosulfuric acid. Peracetic acid, 3-chloroperbenzoic acid and monperphthalic acid are preferred.

The peracids can also be formed in situ, for example from the corresponding acids or acid salts thereof and hydrogen peroxide. The iminopercarboxylic acids in particular are usually prepared in situ, for example from the corresponding nitriles and hydrogen peroxide, preferably in the presence of a weakly acid buffer, for example potassium hydrogen phosphate.

The reaction is usually carried out in a suitable solvent, such as a halogenated hydrocarbon, for example methylene chloride or chloroform, an ester, such as ethyl acetate, an acid, such as acetic acid, for example in the form of glacial acetic acid, or an alcohol, such as a lower alkanol, for example ethanol, at temperatures between about 0° and about 100° C., if appropriate in an inert gas atmosphere and if appropriate under pressure, for example up to about 10 bar.

The acyloxylating decarboxylation which takes place with the introduction of the acyl groups $R_3$—C(=O)— or $R_4$—C(=O)— of a compound of the formula IIb is carried out in a manner known per se, for example by treatment with lead(IV) acylates or by means of anodic oxidation in the presence of a carboxylic acid. The acyl radicals in this lead(IV) acylate correspond to the radicals $R_3$—C(=O)— or $R_4$—C(=O)—, and the carboxylic acid present in the anodic oxidation corresponds to the acids of the formula $R_3$—C(=O)—OH or $R_4$—C(=O)—OH; i.e. in an intermediate product of the formula III which is prepared from a starting material of the formula IIb, the radicals $R_3$ and $R_4$ are identical. Suitable lead(IV) acylates are the corresponding lower alkanoates which are unsubstituted or substituted, for example by halogen, such as fluorine, for example lead tetraacetate, lead tetrapropionate or lead tetra-(trifluoroacetate), or benzoates which are unsubstituted or substituted, for example, by lower alkyl, such as methyl, lower alkoxy, such as methoxy, and/or halogen, such as fluorine or chlorine, for example lead tetrabenzoate. These reagents are used in a customary manner, for example in the presence of a suitable solvent, such as an inert, polar solvent, for example tetrahydrofuran, dioxane, acetic acid, dimethylformaniide, N-methylpyrrolidone or hexamethylphosphoric triamide, or a mixture of solvents, if necessary with the addition of an alkali metal acylate, for example sodium acetate or potassium acetate, and/or an amine, for example pyridine or lutidine, with cooling or heating, for example at temperatures from about 20° C. to about 80° C. and/or in an inert gas atmosphere, for example an argon atmosphere.

The anodic oxidation is usually carried out in a monocell or in a divided cell having a mechanical diaphragm and being composed, for example, of porous clay, glass or polyvinyl chloride, or having an ion exchanger diaphragm, for example a diaphragm obtainable under the trade name Nafion ®, and electrodes made of noble metal, such as platinum, titanium alloys, for example titanium-iridium or titanium-tantalum, and also nickel, lead dioxide, glassy carbon and/or graphite. The reaction is carried out in the presence of an acylate donor, such as an acetate donor, for example in acetic acid or in a mixture of acetic acid and an inert organic solvent, such as acetonitrile, dioxane or dimethylformamide, with the addition of an amine, such as a tri-lower alkylamine, for example triethylamine or tri-n-butylamine, or pyridine, and/or an alkali metal acylate, for example sodium acetate or potassium acetate, and, if desired, an additional so-called conductive salt which increases the conductivity, for example a lithium, sodium, potassium or tetraalkylammonium salt, for example the corresponding tetrafluoborate. Suitable current densities for the electrolysis are between about 10 and about 400 $mA/cm^2$, for example about 40 $mA/cm^2$. The reaction temperature is between about 0° and about 50° C., preferably between room temperature and about 30° C.

Both the reaction with a lead(IV) acylate and the anodic oxidation in the presence of an acylate donor preferably result in a compound of the formula III in which the 1-hydroxyalkyl group at the C(3) ring carbon atom and the acyloxy group at the C(4) ring carbon atom are arranged in the transposition to one another, i.e. result in a diastereomer having the (3R,4R) or the (3S,4S) configuration.

The selective removal of the acyl group $R_4$—C(=O)— in an intermediate of the formula III with the formation of the hydroxyl group is preferably carried out by means of enzymatic ester cleavage. Known esterases which are particularly suitable for cleaving esteritied primary hydroxyl groups are used in this reaction. Thus, for example, for removing an acetyl group in an intermediate of the formula III in which $R_4$ is methyl, it is preferred to use the esterase from *Nocardia mediterranei*, an organism used for the preparation of rifamycin (Schär et al., Appl. Microbiol. Biotechnol. Volume 27, page 451 (1988)). A benzoyloxy group in an intermediate of the formula III in which $R_4$ is phenyl is cleaved, for example, by means of cholesterol esterase (Sigma C9530 from porcine pancreas, which is commercially available).

The reaction is carried out in a manner known per se, preferably under neutral conditions, for example in a suitable aqueous phosphate buffer solution, and at temperatures from about 10° C. to about 30° C., usually at room temperature.

The removal of the hydroxymethyl group which is a substituent on the ring nitrogen atom can be effected in a manner known per se, for example by hydrolysis or by treatment with an acid reagent, preferably after prior oxidation of the hydroxymethyl group to the formyl group.

The latter reaction can be carried out, for example, by treating a compound of the formula IV with a suitable oxidizing metal compound, such as an appropriate chromium(VI) compound, for example chromium(VI) oxide, or an analogous oxidizing agent, preferably under the conditions of the Killiani oxidation, for example using an approximately 8N solution of chromium trioxide in aqueous sulfuric acid.

The removal of the N-hydroxymethyl or, in particular, the N-formyl group can preferably be carried out under acid conditions, using primarily inorganic acids, such as mineral acids, for example hydrochloric acid or sulfuric acid, usually in the form of dilute, aqueous solutions, and also organic carboxylic or sulfonic acids, for example p-toluenesulfonic acid. The N-formyl group, which can, for example, also be removed by treatment with an acid aluminum oxide, for example under the conditions of chromatography, can also be removed under mild basic conditions, for example in the presence of an alkali metal hydroxide, carbonate or bicarbonate or alkaline earth metal hydroxide, carbonate or bicarbonate, which is usually present in aqueous solution.

The hydrolytic removal of the N-hydroxymethyl or N-formyl group is usually carried out at room temperature or at a slightly elevated temperature, for example between about 15° C. and about 50° C., it being possible, in a given case, additionally to use organic solvents, such as suitable alcohols, for example water-soluble lower alkanols, or ether compounds.

In a compound of the formula I which can be obtained in accordance with the invention, and also in an intermediate at any stage of the process according to the invention, the removal of a protective group $R_2'$ can be effected in a manner known per se, for example by solvolysis, such as acidolysis, reduction or oxidation.

An acyl group $R_2'$ can be removed under acid or mild alkaline conditions, depending on the meaning of $R_2'$, for example by treatment with acids, such as formic or trifluoroacetic acid, or with bases, such as an alkali metal hydroxide, carbonate or bicarbonate, for example sodium bicarbonate, a bicyclic amidine, such as 1,5-diazabicyclo[5.4.0]undec-5-ene, or an alkali metal halide.

Certain acyl radicals of half-esters of carbonic acid, such as halogeno-lower alkoxycarbonyl and benzyloxycarbonyl which is unsubstituted or substituted by nitro, can be removed and replaced by hydrogen by reduction, for example by means of catalytic hydrogenation in the presence of a suitable hydrogenation catalyst, for example platinum oxide or palladium, or by fretment with chemical reducing agents, such as zinc in the presence of aqueous acetic acid.

The removal of a lower alkenyloxycarbonyl group in which lower alkenyl is especially allyl can preferably be effected by treatment with a lower alkenyl group acceptor in the presence of a suitable catalyst, such as a metallic phosphine compound, for example tetrakistriphenylphosphine palladium, if appropriate in the presence of triphenylphosphine. Examples of suitable acceptors for lower alkenyl groups, such as the allyl group, are amines, in particular sterically hindered amines, for example tert-butylamine, and also tri-lower alkylamines, for example triethylamine, morpholine or thiomorpholine, and also aliphatic or cycloaliphatic β-dicarbonyl compounds, for example acetylacetone, ethyl acetoacetate or, preferably, dimedone, and also lower alkanecarboxylic acids, for example acetic acid or propionic acid. The reaction is usually carried out by treating the compound of the formula I having a suitably protected hydroxyl group with 1.5 to 10 molar equivalents of the lower alkenyl group acceptor in the presence of 2 to 10 mol %, in particular 5 to 8 mol % (relative to the starting compound), of the catalyst, in particular tetrakistriphenylphosphine palladium catalyst, if appropriate in the presence of up to 50 mol % of triphenylphosphine, in an inert solvent, such as an ether, for example dioxane or especially tetrahydrofuran, a halogenated hydrocarbon, for example methylene chloride, a lower alkanol, for example ethanol, an ester, for example ethyl acetate, or a mixture of such solvents, at temperatures from about 0° C. to about 400° C., preferably at about 20° to about 25° C., and, if necessary, in an inert gas atmosphere, such as an atmosphere of nitrogen or argon.

A 2-oxacycloalkyl or 2-thiacycloalkyl group $R_2'$ can be removed by treatment with an acid, such as a mineral acid, for example hydrochloric or sulfuric acid.

A silyl group $R_2'$ which is substituted as indicated can be removed in the presence of suitable, preferably polar, solvents, such as solvents containing hydroxyl groups, if appropriate under acid conditions or, in particular, by treatment with a salt of hydrofluoric acid which affords fluoride anions, such as an alkali metal fluoride, for example sodium fluoride, if appropriate in the presence of a macrocyclic polyether ("crown ether"), or with the fluoride of an organic quaternary base, such as a tetra-lower alkylammonium fluoride, for example tetrabutylammonium fluoride, if appropriate in the presence of an acid reagent.

In a compound of the formula I obtainable in accordance with the invention, and also in an intermediate at any stage of the process, in which $R_2$ is hydrogen, the free hydroxyl group can be protected in a manner known per se, it being possible, if necessary, to protect temporarily an unsubstituted ring nitrogen atom. The protective group can be introduced, for example, by treatment with a suitable halogenosilane, for example a tri-lower alkyl halogeno silane, such as trimethylchlorosilane or dimethyltert-butylchlorosilane, or a suitable silazane compound, such as hexamethyldisilazane, or by treatment with a reactive derivative of an acid whose acyl radical acts as a hydroxyl protective group, for example by reaction with an anhydride, for example trifluoroacetic anhydride, a mixed anhydride, for example an acid halide, such as 2,2-dichloroacetyl chloride, or a mixed anhydride of a carbonic acid half-ester, for example 2,2,2-trichloroethyl, allyl, phenyl or p-nitrophenyl chlorofortnate, or by reaction with 1,2-dihydrofuran or 1,2-dihydropyran in the presence of an acid, for example p-toluenesulfonic acid.

The present invention preferably relates to a process for the preparation of compounds of the formula I in which $R_1$ is hydrogen or, in particular, methyl, $R_2$ is hydrogen or a hydroxyl protective group $R_2'$, such as the acyl radical of a carbonic acid half-ester, for example 2,2,2-trichloroethoxycarbonyl, allyloxycarbonyl, benzyloxycarbonyl or p-nitrobenzyloxycarbonyl, the acyl radical of a substituted or unsubstituted benzoic acid, for example 4-nitrobenzoyl or 3,5-dinitrobenzoyl, or, in particular, tri-lower alkylsilyl, for example trimethylsilyl, tert-butyldimethylsilyl, or dimethyl-(2,3-dimethyl-2-butyl)-silyl, and $R_3$ is phenyl or methyl, and in which the 1'-C atom of the side chain can have the S configuration or preferably the R configuration, if $R_1$ is methyl.

The invention relates primarily to a process for the preparation of (3R,4R,1'R)-4-acetoxy-3-(1'-hydroxyethyl)-azetidin-2-one or (3R,4R,1'R)-4-benzoyloxy-3-(1'- hydroxyethyl)-azetidin-2-one and their 1'-O-tri-lower alkylsilyl derivatives, such as 1'-O-tert-butyldimethylsilyl or 1'-O-dimethyl-(2,3-dimethyl-2-butyl)-silyl derivatives.

Compounds of the formula I, particularly those in which $R_1$ is hydrogen or methyl, $R_2$ is hydrogen or a hydroxyl protective group $R_2'$ and $R_3$ is methyl or phenyl are valuable intermediates which can be processed further in a manner known per se to give penem or carbapenem compounds which have an antibiotic activity. Further processing is carried out analogously to that of known azetidinone compounds of the formula I in which $R_3$ is methyl, for example as described by T. Hayashi et al., Chem. Pharm. Bull. 29, 3158, 1981, or in European Published Patent Applications No. 42,026 (for penems) or No. 78,026 (for carbapenems).

The starting materials and intermediates used in the process according to the invention are in part novel. They can be prepared in a manner known per se.

Thus, for example, compounds of the formula II (a and b) can be obtained by d) cyclizing the carbanion of a compound of the formula

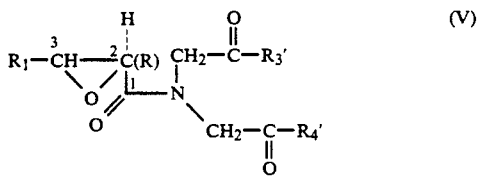

in which $R_3'$ has the meaning of $R_3$ or is etherified hydroxyl, and $R_4'$ has the meaning of $R_4$ or is etherified hydroxyl, $R_3'$ and $R_4'$ either having the meanings of $R_3$ and $R_4$, respectively, or both being etherified hydroxyl, and in which, if $R_1$ is lower alkyl, the 3-C atom has the R configuration or the S configuration, or the carbanion of a compound of the formula

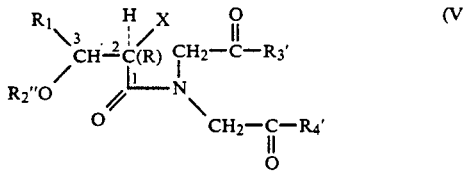

in which $R_2''$ is a hydroxyl protective group which cannot be removed under the conditions of the cyclization process and X is a nucleofugic leaving group and, if $R_1$ is lower alkyl, the 3-C atom has the R configuration or the S configuration, or e) by isomerizing a cis-compound of the formula

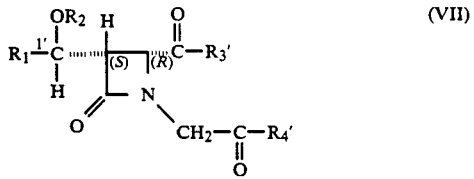

and, if desired, converting a compound of the formula II obtainable in accordance with the invention into another compound of the formula II.

In a starting material of the formula VI a hydroxyl protective group $R_2''$ which cannot be removed under the conditions of the cyclization process is one of the acyl groups mentioned under $R_2'$ of a substituted carboxylic or sulfonic acid, for example 2,2,2-trifluoroacetyl, and also the acyl radical of a carbonic acid halfester, for example p-nitrobenzyloxycarbonyl, or 2-tetrahydrofuryl or 2-tetrahydropyranyl, and also 1-lower alkoxy-lower alkyl, for example methoxymethyl or 1-ethoxyethyl, or substituted or unsubstituted aroyl, for example 4-nitrobenzoyl or 3,5-dinitrobenzoyl. A suitable nucleofugic leaving group X is preferably reactive esterified hydroxyl, for example halogen, for example chlorine, bromine or iodine, lower alkanoyloxy, such as acetoxy, arylsulfonyloxy, for example phenylsulfonyloxy or p-toluenesulfonyloxy, or lower alkylsulfonyloxy, for example methanesulfonyloxy.

An etherified hydroxyl group $R_3'$ or $R_4'$ is, in particular, a hydroxyl group which is etherified with an aliphatic, aromatic or araliphatic radical, such as lower alkoxy, for example methoxy, ethoxy, n-propoxy, isopropoxy or primarily tert-butoxy, aryloxy, for example phenoxy, or aryl-lower alkoxy, for example benzyloxy.

In carbanions of compounds of the formula V or VI the negative charge on the carbon atom is located in the α-position relative to the group of the formula $-CO-R_3'$; i.e. the corresponding compound has the partial formula $>N-CH^{\ominus}-CO-R_3'$. Carbanion compounds of this type are prepared in situ by treating a compound of the formula V or VI in a suitable solvent with a base which forms carbanions, in the course of which the cyclization of process d) takes place. Bases of this type are, inter alia, alkali metal bases, for example sodium hydroxide or carbonate, potassium hydroxide or carbonate or lithium hydroxide or carbonate, or organic alkali metal compounds, for example lower alkyllithium, such as n-butyllithium or tert-butyllithium, alkali metal amides, for example lithium diisopropylamide or di-tert-butylamide, and especially alkali metal amides in which two hydrogen atoms have been replaced by organic silyl groups, for example trimethylsilyl groups, for example lithium bis-(trimethylsilyl)-amide, sodium bis-(trimethylsilyl)-amide or potassium bis-(trimethylsilyl)-amide, inter alia lithium hexamethyldisilazide, and also suitable organic nitrogen bases, such as cyclic amidines, for example 1,5-diazabicyclo-[4.3.0]non-5-ene or 1,5-diazabicyclo[5.4.0]undec-5-ene, and also fluorine compounds which release fluoride ions in an aprotic, organic solvent and which are particularly suitable for the preparation of carbanions of compounds of the formula V, preferably tetralower alkylammonium fluorides, especially tetra-n-butylamonium fluoride.

If a suitable silyl reagent, for example lithium hexamethyldisilazide, is used for the cyclization of a compound of the formula V or VI, under certain circumstances, for example if the reaction is carried out carefully, a compound of the formula IIa in which $R_2$ is a silyl protective group, for example trimethylsilyl, can be obtained directly.

Examples of solvents suitable for the formation of carbanions are halogenated or nonhalogenated hydrocarbons, such as benzene, toluene, methylene chloride or chloroform, ethers, such as dioxane, tetrahydrofuran or dimethoxyethane, amides, such as dimethylforrnamide or hexamethylphosphoric triamide, sulfoxides, such as dimethyl sulfoxide, or nitriles, such as acetonitrile, or mixtures thereof. The reaction can also be carried out under phase transfer conditions, for example in a system consisting of methylene chloride and 50% aqueous sodium hydroxide solution in the presence of a phase transfer catalyst, such as benzyltriethylammonium chloride or tetrabutylammonium bisulfate. The reaction temperature, which depends, inter alia, on the choice of the base used, is between about −80° C. and about 80° C., the reaction being preferably conied out under an inert gas atmosphere, for example an atmosphere of argon or nitrogen.

Under the conditions of the process, an inversion of the configuration at the 2-C atom of the starting material takes place, so that a 3S compound of the formula IIa is formed from a 2R compound of the formula V or VI; the configuration of the 1'-C atom in the side chain, if $R_1$ is lower alkyl, remains unchanged. For example, 3S azetidinones of the formula IIa are obtained from R-glycidamides of the formula V, or (3S, 1'R)-3-hydroxyethylazetidinones of the formula IIa are obtained from (2R,3R)-2,3-epoxybutyramides of the formula V.

The isomerization of a compound of the formula VII (process variant e) can be carried out in a suitable solvent or solvent mixture in the presence of a base. Suitable solvents and bases, and also the reaction conditions, are the same as those which can be used for the cyclization process d). It is preferred to employ aprotic dipoler solvents, such as dimethylforinarnide, N-methylpyrrolidone or dimethyl sulfoxide, and, as bases, in particular potassium carbonate or 1,5-diazabicyclo[5.4.0]undec-5-ene, and it is also possible to carry out the reaction under the phase transfer conditions described.

Starting materials of the formula IIb can be obtained in a manner known per se, for example by solvolysis, from diesters of the formula IIb obtainable in accordance with the invention. The corresponding diester compounds can be converted into the free dicarboxylic acid compounds, for example by means of acid or basic hydrolysis, a di-tertbutyl ester ($R_3' = R_4' =$ tert-butoxy) can, for example, be converted by treatment with dilute, for example 1N, sodium hydroxide solution into a lower alkanol, for example methanol or ethanol, or with trifluoroacetic acid with the application of heat.

The cis-compounds of the formula VII can be formed as byproducts in the course of the cyclization reaction (d) and can be separated off from the products of the desired configuration in a customary manner, for example by means of chromatography.

Compounds of the formula V can be obtained in a manner known per se, for example by reacting an epoxy acid compound of the formula

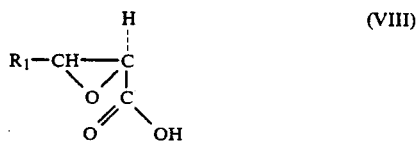

(VIII)

or a suitable salt thereof with an amine compound of the formula

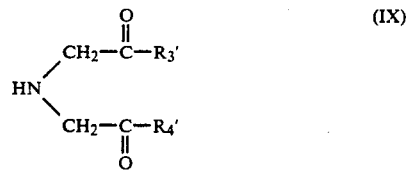

(IX)

The reaction can be carried out under conditions which are analogous to those of the process described in detail below for the preparation of compounds of the formula VIa. The compounds of the formula VIII are known or can be prepared by processes known per se.

The starting materials of the formula V are preferably prepared in situ under the abovementioned carbanion-forming conditions and with a Walden inversion at the 2-C atom from compounds of the formula

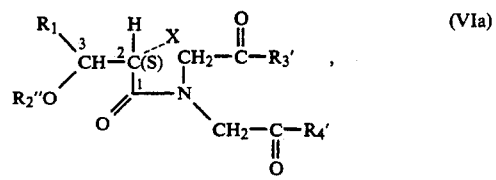

(VIa)

in which $R_2'''$ is hydrogen or a hydroxyl protective group which can be removed under the conditions of epoxide formation and in which, if $R_1$ is lower alkyl, the 3-C atom has the R configuration or the S configuration, the elements of a compound of the formula $R_2'''$-x being removed.

In a compound of the formula VIa a hydroxyl protective group $R_2'''$ which can be removed under the conditions of epoxide formation is a tri-lower alkylsilyl group, for example dimethyltert-butylsilyl or trimethylsilyl. X is preferably halogen, for example chlorine or bromine, lower alkanesulfonyloxy, for example methanesulfonyloxy, or arylsulfonyloxy, for example p-toluenesulfonyloxy.

The removal of $R_2'''$-x in which $R_2'''$ is hydrogen is effected in the course of the treatment with one of the carbanion-forming bases mentioned, for example sodium hydroxide or carbonate or potassium hydroxide or carbonate, preferably with an amidine, for example 1,5-diazabicyclo[5.4.0]undec-5-ene or with a tetra-lower alkylammonium fluoride, for example dehydrated tetra-n-butylammonium fluoride, for example under the reaction conditions described by Djerassi et al., "Steroid Reactions", page 606 (Holden Day, San Francisco, 1963). If $R_2'''$ is, for example, a tri-lower alkylsilyl group which can be removed under the conditions of epoxide formation, it is preferred to use a tetra-lower alkylammonium fluoride.

The reaction of a compound of the formula VIa to give an epoxy compound of the formula V is preferably carried out in an inert solvent or solvent mixture, usually anhydrous, if necessary with cooling or heating, for example within a temperature range from about −40° C. to about +100° C., preferably from about −10° C. to about +50° C., and/or under an inert gas atmosphere, for example an atmosphere of nitrogen.

In the course of this process the configuration at the 2-C atom is inverted, whereas the configuration of the 3-C atom, if $R_1$ is lower alkyl, is retained. Thus the (2R,3R) compounds of the formula V are formed from 2S-halogeno-3R-hydroxy compounds of the formula VIa and the (2R,3S) compounds of the formula V are formed from 2S-halogeno-3S-hydroxy compounds.

After it has been prepared, the epoxide of the formula V can, if desired, be isolated by the removal of $R_2'''$-X from a compound of the formula VIa by employing the amidine used as the reagent in approximately equimolar amounts.

The above compounds of the formula VIa can be prepared, for example, by reacting a compound of the formula

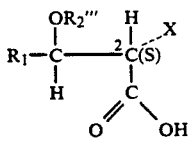

or a reactive functional derivative thereof with an amine of the formula IX. This reaction can be carried out in a manner known per se, for example by subjecting the two reactants to a condensation reaction with one another in the presence of a condensing agent, and dehydrating the free acid, for example in the presence of carbodiimides, such as diethylcarbodiimide, diisopropylcarbodiimide or dicyclohexylcarbodiimide, or di-(N-hetero-cyclyl)-carbonyl compounds, such as carbonyldiimidazole, or 1,2-oxazolium compounds, such as 2-ethyl-5-phenyl- 1,2-oxazolium 3-sulfonate or 2-tert-butyl-5-methyl-1,2-oxazolium perchlorate, which are used in the presence of an inert solvent, such as dimethylformamide, if necessary at a slightly reduced or elevated temperature. Reactive functional derivatives of a carboxylic acid of the formula X are primarily anhydrides, in particular mixed anhydrides, such as the corresponding carboxylic acid chloride or bromide, which are preferably formed in situ by reacting a salt, for example the dicyclohexylamine salt of epoxy acids of the formula VII with suitable halogenating agents, such as phosphorus oxychloride or thionyl chloride, in particular with oxalyl chloride, and which are, if appropriate, reacted with the amine of the formula IX in the presence of a base, for example N-methylmorpholine.

The compounds of the formula VI can be prepared analogously, starting from compounds of the formula IX and from compounds of the formula

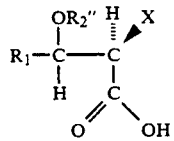

Compounds of the formula X and Xa in which X is halogen are known. They can be prepared, for example, in a manner known per se from L-serine or L-threonine or the D-isomers thereof by diazotizing the amino group with a nitrite salt, for example potassium nitrite, in the presence of a hydrohalic acid.

If L-serine is used and compounds of the formula VI are the starting material, it is possible to obtain compounds of the formula I in which the carbon in the 3-position of the azetidinone ring has the R-configuration. If L-threonine is used, compounds of the formula I in which the C atom in the 3-position of the azetidinone ring has the Reconfiguration and the 1'-C atom of the hydroxyethyl side chain ($R_1$ is methyl) has the R-configuration. If it is intended to prepare compounds of the formula I in which the 3-C atom has the R-configuration and the 1'-C atom, for example, of a 1-hydroxyethyl side chain has the S-configuration, allothreonine is used as the starting material. In all the reactions described the configuration of the C atom which in compounds of the formula I corresponds to the 1'-C atom of a 1-$OR_2$-lower alkyl side chain having more than one carbon atom in the lower alkyl moiety remains unchanged.

Amines of the formula DC, in particular the amines having symmetrical substituents, are known or, if novel, can be prepared in a manner known per se. Thus, for example, a compound of the formula IX in which $R_3'$ and $R_4'$ are tert-butoxy can be prepared by the action of isobutylene on the corresponding acid, usually in dioxane in the presence of 95–98% sulfuric acid at room temperature. A preferred process for the preparation of compounds of the formula IX in which $R_3'$ and $R_4'$ represent phenyl consists in reacting a phenacylamine hydrochloride with a phenacyl chloride or phenacyl bromide in the presence of a suitable base, for example triethylamine, and in methylene chloride.

The present invention also embraces embodiments of the process in which the starting material is a compound obtainable at any preliminary stage of the process and the subsequent process stages are carried out. It also embraces a combination of process steps, for example starting from one of the compounds of the formula VI to X to give a compound of the formula I or starting from one of the compounds of the formulae IX or X or Xa to give a compound of the formula VI or IVa, respectively.

The process according to the invention has the advantage that the compounds of the formula I can be prepared stereospecifically in a high yield and in an economical manner, and that it is possible to use the readily accessible and cheap symmetrically substituted amines of the formula IX, whose substituents serve on the one hand for the cyclization to give the β-lactam compounds and on the other hand as a temporary N-protective group which can be removed under mild conditions.

The following examples serve to illustrate the invention. Temperatures are in degrees centigrade. The specific angles of rotation are $[\alpha]_D^{20}$ values. Columns packed with Merck silica gel 60 can be used for the separation by chromatography in preparative work-up.

EXAMPLE 1

1.1. A solution of 0.866 g of (3S,4S,1'R)-4-benzoyl-3-(1'-hydroxyethyl)-1-phenacylazetidin-2-one and 5.7 g of 3-chloroperbenzoic acid in 30 ml of methylene chloride is stiffed for 8 hours at room temperature. The white suspension is diluted with methylene chloride and washed successively with a 5% aqueous solution of sodium thiosulfate/potassium iodide, water, aqueous sodium bicarbonate solution and water, dried and evaporated under a water pump vacuum. The crude product is purified by means of medium pressure chromatography (solvent: a 2:3 mixture of hexane and ethyl acetate). After the main fraction has been recrystallized from methylene chloride/diethyl ether, (3R,4R,1'R)-4-benzoyloxy-1-benzoyloxymethyl-3-(1'-hydroxy-ethyl)-azetidin-2-one is obtained, melting point 136°–138°.

1.2. 0.06 g of imidazole and 0.088 g of tert-butyldimethylchlorosilane are added to a solution of 0.18 g of (3R,4R, 1'R)-4-benzoyloxy-1-benzoyloxymethyl-3-(1'-hydroxyethyl)-azetidin-2-one in 1 ml of dimethylformamide and the mixture is stirred for 24 hours at room temperature. A further 0.015 g of imidazole and 0.022 g of tert-butyldimethylchlorosilane are added to the reaction mixture, which is stirred for a further 6 hours at room temperature and then discharged onto ice and a saturated aqueous solution of sodium bicarbonate, the product is taken up in diethyl ether, and the organic phase is washed once each with aqueous sodium bicarbonate solution, 1% aqueous citric acid, water, aqueous sodium bicarbonate solution and water. The aqueous phases are washed again with diethyl ether; the combined organic extracts are dried with sodium sulfate and evaporated in a water pump vacuum. The crude product is dissolved in a 3:2 mixture of hexane and ethyl acetate and is filtered through silica gel 60. Recrystallization from methylene chloride/diethyl ether gives pure (3R,4R,1'R)-4-benzoyloxy-1-benzoyloxymethyl-3-[1'-(tert-butyl dimethylsilyloxy)-ethyl]-azetidin-2-one, melting point 109°–110°; $[\alpha]_D = -14.1°$ (c=0.545% in chloroform).

1.3. 0.03 g (30 U) of cholesterol esterase (Sigma C9530, from porcine pancreas) is dissolved in 33 ml of phosphate buffer pH 7 in a 50 ml round-bottomed flask controlled by thermostat at 30°, and 0.05 g of (3R,4R, 1'R)-4-benzoyloxy-1-benzoyloxymethyl-3-[1'-(tert-butyl dimethylsilyloxy)-ethyl]-azetidin-2-one, dissolved in 6 ml of acetone, is added in portions in the course of 10 hours. The reaction is followed by thin layer chromatography (solvent: a 1:1 mixture of ethyl acetate and hexane) and by high pressure liquid chromatography (solvent: an 85:15 mixture of acetonitrile and water). After 20 hours, the reaction mixture is extracted with six times 100 ml each of chloroform. The organic extract gives a slightly yellow oil which, according to high pressure liquid chromatography, still contains about 10% of starting material. Chromatography over silica gel (mobile phase: a 4:1 mixture of methylene chloride and ethyl acetate) gives (3R,4R,1'R)-4-benzoyloxy-1-hydroxy-methyl-3-[1'-(tert-butyldimethylsilyloxy)-ethyl]-azetidin-2-one, which, after recrystallization from methylene chloride/diethyl ether/hexane, melts at 83°–85°; $[\alpha]_D = +68.5°$ (c=0.672% in chloroform).

1.4. 0.21 ml of 8N chromosulfuric acid (Killiani mixture) is added to a solution of 0.16 g of (3R,4R,1'R)-4-benzoyloxy-1-hydroxymethyl-3-[1'-(tert-butyldimethylsilyloxy)-ethyl]-azetidin-2-one in 10 ml of methylene chloride, and the mixture is stirred for 5 hours at room temperature. Excess oxidizing agent is destroyed by adding 1 ml of isopropanol, and the reaction mixture is applied directly to a column of 80 g of aluminum oxide (Alox II, acid) and eluted with ethyl acetate. This gives virtually pure (3R,4R, 1'R)-4-benzoyloxy-3-[1'-tert-butylidimethylsilyloxy)-ethyl]-azetidin-2-one, melting point 125°–126°; $[\alpha]_D = 71.1°$ (c=0.85% in chloroform), after recrystallization from diethyl ether/hexane. (3R,4R,1'R)-4-Benzoyloxy-3-(1'-hydroxyethyl)-azetidin-2-one, melting point 145°–1470° (from methylene chloride/diethyl ether) can be obtained from the (3R,4R, 1'R)-4-benzoyloxy-3-[1'-(tert-butylsimethylsilyloxy)-ethyl]-azetidin-2-one by treatment with tetrabutylammonium fluoride trihydrate in tetrahydroluran and acetic acid.

The starting material can be prepared as follows:

1.5. A solution of 2.7 nil of oxalyl chloride in 8.5 ml of methylene chloride is added dropwise, in the course of 15 minutes, to a mixture of 6.86 g of dimethylfonnamide and 40 ml of methylene chloride, cooled to −25°. The white suspension is stirred for a further 20 minutes at −25°, and a solution of 9.87 g of the dicyclohexylammonium salt of (2R,3R)-2,3-epoxgfityric acid in 40 ml of methylene chloride is then added in the course of 10 minutes. The reaction mixture is stirred for a further 20 minutes at the same temperature and 8.7 ml of triethylamine are then added, followed, in portions, by 7.29 g of diphenacylamine hydrochloride. The cooling bath is removed and the reaction mixture is stirred for 21 hours at room temperature. The yellow suspension is then filtered through a sintered glass suction filter and the residue is washed exhaustively with methylene chloride. The filtrate is diluted with methylene chloride and washed successively with water, 5% aqueous citric acid, saturated aqueous sodium bicarbonate solution and water. The aqueous phases are subsequently extracted twice with methylene chloride, and the combined organic phases are dried over sodium sulfate and evaporated under a water pump vacuum. The resulting crude product is purified by flash chromatography over 750 g of silica gel (Merck 9385; mobile phase: a 2:1 mixture of hexane and ethyl acetate), and (2R,3R)-2,3-epoxy-N,N-bis-phenacylbutyramide is obtained in the form of a yellowish oil.

1.6. A solution of 3.48 g of (2R,3R)-2,3-epoxy-N,N-bis-phenacylbutyramide in 100 ml of tetrahydrofuran is cooled with stirring to −15°, and 20.6 ml of a 0.5-molar solution of lithium hexamethyldisilazide in tetrahydrofuran is added at a temperature between −10° and −15°; the reaction is complete after stirring for about 4 hours within the same temperature range. The dark red reaction mixture is poured onto 100 ml of an ice cold buffer solution (pH 6.0) and the product is extracted three times with methylene chloride. The organic extracts are washed with saturated aqueous sodium chloride solution, dried with sodium sulfate and evaporated under a water pump vacuum. The crude product obtained is separated into three constituents by medium pressure chromatography over a 100-fold amount of a silica gel preparation [LiChroprep® Si 60 made by Merck AG, Darmstadt (West Germany); particle size 25–40 μm; mobile phase: a 4:1 mixture of hexane and ethyl acetate]. This gives, as the least polar fraction, (3S,4S,1'R)-4-benzoyl-3-(1'-trimethylsilyloxyethyl)-1-phenacylazetidin-2-one, as the product of medium polarity, (3S,4R,1'R)-4-benzoyl-3-(1'-hydroxyethyl)-1-phenacylazetidin-2-one ("cis-compound") of melting point 128°–129° (from methylene chloride/diethyl ether/hexane) and, finally, amorphous (3S,4S,1'R)-4-benzoyl-3-(1'-hydroxyethyl)-1-phenacylazetidin-2-one.

EXAMPLE 2

2.1. 8.95 g of lead tetraacetate are added under an argon atmosphere and with stirring at room temperature to a solution of 2.9 g of (3S,4S,1'R)-1-carboxymethyl-3-[1'-(tert-butyldimethylsilyloxy)-ethyl]-2-oxoazetidin-4-carboxylic acid in 90 ml of tetrahydrofuran and 13 ml of dimethylformamide. After 75 minutes at 25°, the excess lead tetraacetate is destroyed by adding 2.2 ml of ethylene glycol dropwise, the resulting white suspension is filtered through a silica gel preparation (Hyflo), the residue on the filter is subsequently washed thoroughly with tetrahydrofuran, and the filtrate is evaporated under a water pump vacuum. The oily residue is purified by flash chromatogaphy over 250 ml of silica gel (silica gel 60; 0.040–0.63 mm; mobile phase: a 60:4 mixture of hexane and ethyl acetate). This gives (3R,4R,1'R)-4-acetoxy-1-acetoxymethyl-3-[1'-(tert-butyldi-methylsilyloxy)ethyl]-azetidin-2-one in the form of an oil, $[\alpha]_D = +9.4°$ (c=0.287% in chloroform). (3R,4R,1'R)-4-Acetoxy-1-acetoxymethyl-3-[1'-(dimethyl-(2,3-dimethyl-2-butyl)-silyloxy)-ethyl]-azetidin-2-one is obtained analogously in amorphous form, $[\alpha]_D = +3.3°$ (c=2.1% in chloroform), starting from (3S,4S,1'R)-N-carboxymethyl-3-[1'-(dimethyl-(2,3-dimethyl-2-b utyl)-silyloxy)-ethyl]-2-oxoazetidine-4-carboxylic acid.

2.2. 3 ml of a solution of acetyl esterase (aqueous solution containing 723 U/ml) from Nocardia mediterranei [see: H. P. Schär, D. Gygax, G. M. Ramos Tombo and O. Ghisalba, Appl. Microbiol. Biotechnol., volume 27, page 451 (1988)] are added to 0.92 g of (3R,4R,1′R)-4-acetoxy-1-acetoxymethyl-3-[1′-(tert-butyldimethylsilyloxy)-ethyl]-azetidin-2-one in 70 ml of phosphate buffer of pH 7. The solution is stirred for 24 hours at room temperature, then a further 2 ml of the above enzyme solution are added and after two further days the mixture is extracted with methylene chloride. This gives a crude product which contains only small amounts of the starting material. Purification by chromatography (silica gel; mobile phase: a 96:4 mixture of methylene chloride and methanol) gives (3R,4 R,1′R)-4-acetoxy-1-hydroxymethyl-3-[1′-(tert-butylidimethylsilyloxy)-ethyl]-azetidin-2-one, which crystallizes spontaneously and melts at 51°–53°.

2.3. 2 ml of 8N chromosulfuric acid (Killiani mixture) are added to a solution of 0.317 g (3R,4R,1′R)-4-acetoxy-1-hydroxymethyl-3-[1′-(tert-butyldimethylsilyloxy)-ethyl]-azetidin-2-one in 2 ml of methylene chloride, and the mixture is stirred for 4 hours at room temperature. Stirring is continued for a further 24 hours after adding a further 0.25 ml of chromosulfuric acid. Excess oxidizing agent is destroyed by adding 1 ml of isopropanol, and the reaction mixture is applied directly to a column of 10 g of aluminum oxide (Alox II, acid) and eluted with a 1:1 mixture of hexane and ethyl acetate. This gives (3R,4R,1′R)-4-acetoxy-3-[1′-(tert-butyldimethylsilyloxy)-ethyn-azetidin-2-one, melting point 107°–109° (from low-boiling petroleum ether).

2.4. 0.3 g of (3R,4R,1′R)-4-acetoxy-3-]1′-(tert-butyldimethylsilyloxy)-ethyl]-azetidin-2-one is added with stirring to a solution of 0.63 g of tetrabutylammonium fluoride trihydrate in 10 ml of tetrahydrofuran and 0.8 ml of acetic acid, and the mixture is stirred for 16 hours at room temperature. The reaction mixture is discharged onto ice water and extracted three times with methylene chloride. The combined organic extracts are washed successively with a saturated aqueous solution of sodium bicarbonate and a saturated aqueous solution of sodium chloride, dried over sodium sulfate and evaporated under a water pump vacuum at a bath temperature of 35°. The residue is recrystallized from methylene chloride/diethyl ether/hexane and affords (3R,4R,1′R)-4-acetoxy-3-(1-hydroxyethyl)-azetidin-2-one, melting point 110°–112°.

The starting material can be obtained as follows:

2.5. A solution of 11.6 g of oxalyl chloride in 25 ml of methylene chloride is added dropwise, in the course of 15 minutes, to a mixture, cooled to −25°, of 20 g of dimethylforinaniide and 115 ml of methylene chloride. The white suspension is stirred for a further 20 minutes at −25°, and a solution of 28.5 g of the dicyclohexylammonium salt of (2R,3R,)-2,3-epoxybutyric acid in 115 ml of methylene chloride is then added in the course of 10 minutes. The reaction mixture is stirred for a further 20 minutes at the same temperature, and a solution of 17.87 g of di-tert-butyl iminodiacetate in 90 ml of methylene chloride and 9.22 ml of N-methylmorpholine are then added dropwise simultaneously in the course of 15 minutes. The cooling bath is removed and the reaction mixture is stirred for 3 hours at room temperature. The white suspension is then filtered through a sintered glass suction filer, the residue is washed with methylene chloride, and the filtrate is diluted with methylene chloride and washed successively with water, 5% aqueous citric acid, saturated aqueous sodium bicarbonate solution and water. The aqueous phases are subsequently extracted twice with methylene chloride, and the combined organic phases are dried and evaporated under a water pump vacuum. The yellow-brown crude product is purified by flash chromatography over silica gel (Merck 9385) using a 9:1 mixture of methylene chloride and ethyl acetate as the mobile phase. (2R,3R)-N,N-Bis-(tert-butoxy-carbonylmethyl)-2,3-epoxybutyramide is obtained in the form of a pale yellow oil, $[\alpha]_D = +52°$ (c=1.250% in chloroform).

2.6. A solution of 13.18 g of (2R,3R)-N,N-bis-(tert-butoxycarbonylmethyl)-2,3-epoxybutyramide in 100 ml of tetrahydrofuran is cooled with stirring to −15°, and 100 ml of a 0.5-molar solution of lithium hexamethyldisilazide in tetrahydrofiran is added at temperatures between −15° and −10°. The progress of the reaction is followed by thin layer chromatography (solvent: a 1:1 mixture of hexane and ethyl acetate); the reaction is complete after stirring for about 4 hours at the temperature indicated above. The reaction mixture is diluted with methylene chloride and poured onto ice, and the organic layer is washed successively with water, twice with 0.1N hydrochloric acid, water, saturated aqueous sodium bicarbonate solution and water. The wash water is extracted twice with methylene chloride, and the combined organic phases are dried over sodium sulfate and evaporated under a water pump vacuum. After flash chromatography over 750 g of silica gel 60 (0.040–0.063 mm, Merck; elution with a 6:4 mixture of hexane and ethyl acetate), the crude product obtained gives (3S,4S,1R)-4-tert-butoxycarbonyl-1-tert-butoxycarbonylmethyl-3-(1′-hydroxyethyl)-azetidin-2-one, which melts at 79°–81°; $[\alpha]_D$ −22.6° (c=0.574% in chloroform).

2.7. 2.45 g of imidazole and 3.61 g of tert-butyldimethylchlorosilane are added to a solution of 6.59 g of (3S,4S,1′R)-4-tert-butoxycarbonyl-1-tert-butoxycarbonylmethyl-3(1′-hydroxyethyl)-azetidin-2-one in 25 ml of dimethylformamide, and the mixture is stirred for 6 hours at room temperature. The reaction mixture is discharged onto ice and a saturated aqueous solution of sodium bicarbonate and the product is taken up in diethyl ether. The organic phase is washed once each with aqueous sodium bicarbonate solution, 1% aqueous citric acid, water, aqueous sodium bicarbonate solution and water. The aqueous phases are extracted with diethyl ether, and the combined organic phases are dried over sodium sulfate and evaporated under a water pump vacuum. The crude product is dissolved in an 80:20 mixture of hexane and ethyl acetate, and the solution is filtered through 200 g of silica gel (silica gel 60) to give (3S,4S, 1′R)-4-tert-butoyxcarbonyl-1-tert-butoxycarbonylmethyl-3-[1′-(tert-butyldimethylsilyloxy)-ethyl]-2-one in the form of an oily product, $[\alpha]_D = -14.6°$ (c=0.553% in chloroform).

(3S,3S,1′R)-4-tert-Butoxycarbonyl-1-tert-butoxycarbonylmethyl-3-[1′-(dimethyl-(2,3-dimethyl-2-butyl)-silyloxyethyl]-azetidin-2-one, $[\alpha]_D = -16.8°$ (c=2.5 in chloroform), is obtained analogously using dimethyl-(2,3-dimethyl-2-butyl)-chlorosilane.

2.8. 29.3 ml of 1N aqueous sodium hydroxide solution are added dropwise, with ice cooling, to a solution, cooled to −5°, of 5.4 g of (3S,4S,1′R)-4-tert-butoxycarbonyl-1-tertbutoxycarbonylmethyl-3-[1′-(tert-butyldimethylsilyloxy)-ethyl]-azetidin-2-one in 120 ml of ethanol. The reaction mixture is then stirred for 14 hours at 0° to 5°, then concentrated to a volume of about 30 ml under a water pump vacuum on a rotary evaporator (bath temperature 30°) and extracted twice with ethyl acetate. Ethyl acetate is added to the aqueous phase which has been separated off, and the mixture is again cooled to about 0° to 5°) and adjusted to pH 2.0 by dropwise addition of orthophosphoric acid, with stirring and cooling in ice. The phases are separated, the aqueous layer is extracted three times with ethyl acetate, and the combined organic phases are dried with sodium sulfate and evaporated in a water pump vacuuum. The crude product obtained is crystallized from ethyl acetate/hexane and gives (3S,4S,1′R)-1-carboxymethyl-3-[1′-(tert-butyldimethylsilyloxy)-ethyl]-2-oxoazetidine-4-carboxylic acid, which melts at 134°–135°; $[\alpha]_D = -32.9$ (c=1.058% in chloroform).

The corresponding (3S,4S, 1′R)-1-carboxymethyl-3-[1′-(dimethyl-(2,3-dimethyl-2-butyl)-silyloxy)-ethyl]-2-oxoazetidine-4-carboxylic acid is obtained analogously, starting from (3S,4S,1′R)-4-tert-butoxycarbonyl-1-tert-butoxycarbonylmethy-3-[1′-(dimethyl-(2,3-dimethyl-2-butyl)-silyloxy)-ethyl]-azetidin-2-one.

What is claimed is:

1. A method of using a compound of the formula IIa

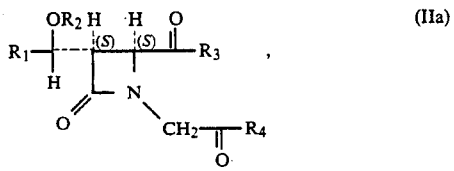

wherein
$R_1$ is hydrogen or lower alkyl;
$R_2$ is hydrogen or a hydroxy protecting group $R_2'$; and
$R_3$ and $R_4$ are identical to each other and are selected from the group consisting of
(i) phenyl,
(ii) phenyl substituted by lower alkoxy, lower alkyl, and/or halogen,
(iii) 4-nitrophenyl, and
(iv) lower alkyl;
which comprises
(a) treating said compound of formula IIa with a peracid to result in a compound of formula III

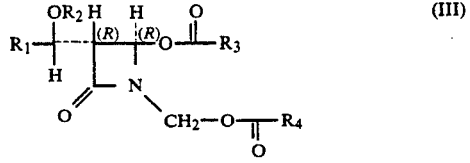

(b) replacing the radical of the formula $R_4$—C(=O)— in formula III by hydrogen by enzymatic ester cleavage to obtain the compound of formula IV

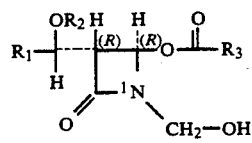

and
(c) removing from the compound of formula IV the hydroxymethyl group in the 1-position, if appropriate after conversion into a formyl group, to result in a compound of formula I

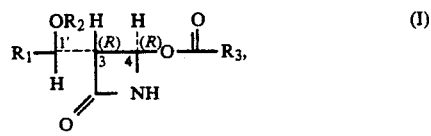

and, if desired, in a compound of formula I thus obtained in which $R_2$ is a protective group $R_2'$, converting the protected hydroxyl group into the free hydroxyl group, and/or if desired in a compound of formula I thus obtained in which $R_2$ is a hydrogen, converting the free hydroxyl group into a protected hydroxyl group.

2. The method of claim 1 wherein said enzymatic ester cleavage is accomplished by an esterase.

3. The method of claim 2 wherein $R_4$ is methyl and said esterase is an esterase from *Nocardia mediterranei*.

4. The method of claim 2 wherein $R_4$ is phenyl and said esterase is a cholesterol esterase.

5. The method of claim 1 wherein
$R_1$ is hydrogen or methyl;
$R_2$ is hydrogen or a hydroxyl protective group; and
$R_3$ is phenyl or methyl.

6. The method of claim 1 wherein said peracid is an organic percarboxylic acid.

7. The method according to claim 1 wherein $R_1$ is methyl and $R_3$ is phenyl so that (3R,4R,1′R)-4-benzoyloxy-3-(1′-hydroxyethyl)-azetidin-2-one or a 1′-O-tri-lower alkylsilyl derivative thereof is prepared as the compound of formula I.

8. The method according to claim 1 wherein $R_1$ and $R_3$ are each methyl so that (3R,4R,1′R)-4-acetoxy-3-(1′-hydroxyethyl)-azetidin-2-one or a 1′-O-tri-lower alkylsilyl derivative thereof is prepared as the compound of formula I.

9. The method of claim 6 wherein said peracid is selected from the group consisting of peracetic acid, 3-chloroperbenzoic acid, and monoperphthalic acid.

10. The method of claim 1 wherein said hydroxymethyl group at position 1 of the compound of formula IV is oxidized to a formyl group by treating said compound of formula IV with a chromium (VI) compound, and said formyl group is removed under acid conditions to yield said compound of formula I.

11. The method of claim 10 wherein said chromium (VI) compound is chromium (VI) oxide.

* * * * *

UNITED STATES PATENT AND TRADEMARK OFFICE
CERTIFICATE OF CORRECTION

PATENT NO. : 5,317,100
DATED : May 31, 1994
INVENTOR(S) : Jaroslav Kalvoda, et al.

It is certified that error appears in the above-indentified patent and that said Letters Patent is hereby corrected as shown below:

Column 18:

In claim 1, line 2, replace the formula IIa with

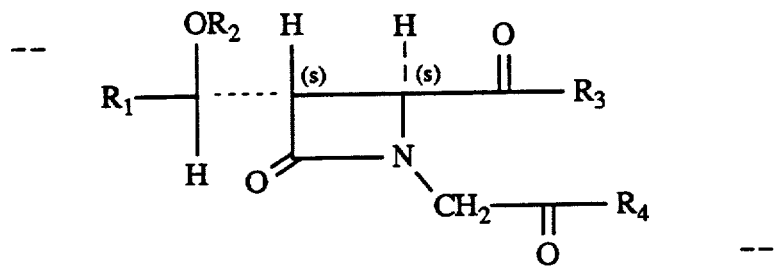

UNITED STATES PATENT AND TRADEMARK OFFICE
CERTIFICATE OF CORRECTION

PATENT NO. : 5,317,100
DATED : May 31, 1994
INVENTOR(S) : Jaroslav Kalvoda, et al.

It is certified that error appears in the above-indentified patent and that said Letters Patent is hereby corrected as shown below:

Column 18:

In claim 8, line 2 after "so that" delete "(3R,4R,1'R)" and insert --(3S,4R,1'R)-- in lieu thereof.

Signed and Sealed this

Eleventh Day of October, 1994

*Attest:*

BRUCE LEHMAN

*Attesting Officer*     *Commissioner of Patents and Trademarks*